United States Patent
Rose

(10) Patent No.: US 7,849,219 B2
(45) Date of Patent: Dec. 7, 2010

(54) COMMUNICATION SYSTEM AND METHOD FOR REAL-TIME INTERNET-BASED NETWORK CONNECTIVITY TO MULTIPLE HETEROGENEOUS BACKEND SYSTEMS

(75) Inventor: Eric A. Rose, Ashland, MA (US)

(73) Assignee: IDX Investment Corporation, South Burlington, VT (US)

(*) Notice: Subject to any disclaimer, the term of this patent is extended or adjusted under 35 U.S.C. 154(b) by 690 days.

(21) Appl. No.: 10/909,018

(22) Filed: Jul. 30, 2004

(65) Prior Publication Data

US 2006/0026300 A1 Feb. 2, 2006

(51) Int. Cl.
G06F 15/16 (2006.01)
(52) U.S. Cl. .................. 709/246; 709/201; 709/202; 709/203; 709/217; 709/226; 709/229; 709/238
(58) Field of Classification Search ................ 709/203, 709/219, 223, 224, 225, 227, 232, 201, 202, 709/217, 226, 238, 246
See application file for complete search history.

(56) References Cited

U.S. PATENT DOCUMENTS

| | | | | |
|---|---|---|---|---|
| 6,775,276 | B1* | 8/2004 | Beser | 370/389 |
| 6,810,429 | B1* | 10/2004 | Walsh et al. | 709/246 |
| 6,886,046 | B2* | 4/2005 | Stutz et al. | 709/246 |
| 7,124,188 | B2* | 10/2006 | Mangipudi et al. | 709/226 |
| 2003/0187641 | A1* | 10/2003 | Moore et al. | 704/235 |
| 2005/0021563 | A1* | 1/2005 | Shaburov | 707/104.1 |
| 2005/0086347 | A1* | 4/2005 | Deen et al. | 709/229 |
| 2005/0223021 | A1* | 10/2005 | Batra et al. | 707/102 |

\* cited by examiner

Primary Examiner—Yves Dalencourt
Assistant Examiner—Barbara N Burgess
(74) Attorney, Agent, or Firm—Andrus, Sceales, Starke & Sawall, LLP

(57) ABSTRACT

A communication system (110) for connecting in real-time an Internet-based network interface (130) to a plurality of backend systems (136), each of the plurality of backend systems having an associated backend communications protocol and requiring an associated backend data format. The system includes a router (112) for receiving a job (124) having a front-end data format and a front-end communications protocol from the Internet-based network interface. The router selects one or more backend systems from the plurality of backend systems as a function of attributes of the job for delivery of the job to the one or more backend systems. The system also includes a plurality of service agents (114, 116, 118), each in communication with an associated one of the plurality of backend systems and configured to translate and reformat the job prior to delivery to the one or more backend systems.

19 Claims, 9 Drawing Sheets

COMMUNICATION SYSTEM AND METHOD FOR REAL-TIME INTERNET-BASED NETWORK CONNECTIVITY TO MULTIPLE HETEROGENEOUS BACKEND SYSTEMS

FIELD OF THE INVENTION

The present invention generally relates to the field of network communication of information. In particular, the present invention is directed to a communication system and method for real-time Internet-based network connectivity to multiple heterogeneous backend systems.

BACKGROUND OF THE INVENTION

The healthcare software market has traditionally been dominated by large, complex, workflow-based applications that help healthcare employees perform their jobs in a more efficient manner. These applications are very good at providing services to the internal staff at the organization that purchased/installed them. However, they are less successful at providing services to people indirectly affiliated with the organization—examples are patients or satellite clinicians who refer in to the large organizations. The applications are simply too complex to provide strong benefit to these affiliated users, who just need high-level or overview information.

With the advent of the Internet, vendors began to see the opportunity to provide applications to reach out to these affiliated users. Web-based products can sit on top of the large core applications, and provide a simpler user interface which has more value to the end user. Vendors connected their web application and their core application, and were able to bring the web applications to market.

As these Internet applications began hitting the market, a new problem emerged. Most healthcare organizations deploy clinical/administrative systems from more than one vendor (best-of-breed approach). As the vendors created their Internet applications, customers found that they would have to deploy separate web-based applications to gain access to data across the enterprise. The affiliated users would have to log into to separate applications to view related data. This clearly was not ideal, and demand rose for a web-based product that would provide a single view over all the data in the enterprise, no matter where it resided.

Vendors attempted to tackle this problem via the use of interfaces. In these interfaces, the web application would not communicate with the large core applications directly. Instead, the web application communicated directly with a duplicated database under its control. That duplicated database was fed information from the core applications via interfaces. This approach allowed the web application to display information from multiple sources, providing the single view that the affiliated users were looking for. However, there are problems with this approach, such as the interfaces are typically non-trivial to maintain—there are support/implementation costs, as well as personnel costs; the web-application-owned database now has a copy of data from other systems with elaborate efforts being made to ensure that the duplicated data is up-to-date, and does not age. For example, if a change is made to data in the core product, that change needs to be uploaded into the web-owned database. Otherwise, users of the web application will view inaccurate data—a critical problem in the healthcare industry. Additionally, the duplicated database typically runs on a less reliable system than that of backend systems and uses a higher level code, that is generally less efficient than the operating system level code of backend systems, for maintaining the duplication of data.

HIPAA regulations govern privacy and security of patient-related healthcare information. All applications displaying such information need to make sure that infrastructure is in place to comply with HIPAA regulations. Since the web application has a database of healthcare data, that application needs to build even more infrastructure to handle the security of that database. The vendor may have to replicate security that already exists in their core application.

SUMMARY OF THE INVENTION

In one embodiment of the present invention, a communication system for connecting in real-time an Internet-based network interface to a plurality of backend systems, each of the plurality of backend systems having an associated backend communications protocol and requiring an associated backend data format. The system includes a router for receiving a job having a front-end data format and a front-end communications protocol from the Internet-based network interface. The router selects one or more backend systems from the plurality of backend systems as a function of attributes of the job for delivery of the job to the one or more backend systems. The system also includes a plurality of service agents, each in communication with an associated one of the plurality of backend systems and configured to translate the job prior to delivery to the one or more backend systems.

In another embodiment of the present invention, a communication system is provided for connecting in real-time an Internet-based network interface to a plurality of backend systems, each of the plurality of backend systems having an associated backend communications protocol and requiring an associated backend data format. The system includes a router for receiving a job having a front-end data format and a front-end communications protocol from the Internet-based network interface, wherein the router selects one or more backend systems from the plurality of backend systems as a function of attributes of the job for delivery of the job to the one or more backend systems; and a plurality of service agents, each of which is associated with a respective one of the plurality of backend systems, wherein each of the plurality of service agents being configured (1) to translate the job received from the router from the front-end data format to the associated backend data format, (2) to translate the job from the front-end communications protocol to the associated backend communications protocol, (3) to communicate the job to the associated one of the plurality of backend systems, (4) to receive a response from the associated one of the plurality of backend systems, (5) to translate the response from the associated backend communications protocol to the front-end communications protocol, (6) to translate the response from the associated backend data format to the front-end data format, and (7) to communicate a translated response to the Internet-based network interface.

In yet another embodiment of the present invention, a communication system is provided for connecting in real-time an Internet-based network interface to a first backend system having a first backend communications protocol and requiring a first backend data format and a second backend system having a second backend communications protocol and requiring a second backend data format. The system includes (a) a router for receiving a job having a front-end data format and a front-end communications protocol from the Internet-based network interface, wherein the router selects one or more backend systems from the plurality of backend systems as a function of attributes of the job for delivery of the job to the one or more backend systems; (b) a first service agent associated with the first backend system and configured (1) to receive the job from the router, (2) to translate the job received from the router from the front-end data format to the first backend data format, (3) to translate the job from the front-end communications protocol to the first backend communications protocol, (4) to communicate the job to the first backend systems, (5) to receive a first response from the first backend systems, (6) to translate the first response from the first backend communications protocol to the front-end communications protocol, (7) to translate the first response from the first backend communications protocol to the front-end communications protocol, and (8) to communicate a first translated response to the Internet-based network interface; and (c) a second service agent associated with the second backend system and operatively configured (1) to receive the job from the router, (2) to translate the job received from the router from the front-end data format to the second backend data format, (3) to translate the job from the front-end communications protocol to the second backend communications protocol, (4) to communicate the job to the second backend systems, (5) to receive a second response from the second backend systems, (6) to translate the second response from the second backend communications protocol to the front-end communications protocol, (7) to translate the second response from the second backend communications protocol to the front-end communications protocol, and (8) to communicate a second translated response to the Internet-based network interface.

In still another embodiment of the present invention, a method is provided for communicating in real-time between an Internet-based network interface and a plurality of backend systems, each of the plurality of backend systems having an associated backend communications protocol and requiring an associated backend data format. The method includes receiving a job having a front-end communications protocol and a front-end data format from the Internet-based network interface; selecting one or more backend systems from the plurality of backend systems as a function of attributes of the job for delivery of the job to the one or more backend systems; delivering the job to each of the one or more backend systems in the associated backend communications protocol and associated backend data format for each of the one or more backend systems; translating a response from each of the one or more backend systems from the associated backend communications protocol to the front-end communications protocol and from the associated backend data format to the front-end data format; and delivering a translated response to the Internet-based network interface.

In still yet another embodiment of the present invention, a computer readable medium having computer-executable instructions for communicating in real-time between an Internet-based network interface and a plurality of backend systems, each of the plurality of backend systems having an associated backend communications protocol and requiring an associated backend data format is provided. The computer-executable instructions, when executed by the computer, include receiving a job having a front-end communications protocol and a front-end data format from the Internet-based network interface; selecting one or more backend systems from the plurality of backend systems as a function of attributes of the job for delivery of the job to the one or more backend systems; delivering the job to each of the one or more backend systems in the associated backend communications protocol and associated backend data format for each of the one or more backend systems; translating a response from each of the one or more backend systems from the associated backend communications protocol to the front-end communications protocol and from the associated backend data format to the front-end data format; and delivering a translated response to the Internet-based network interface.

In a further embodiment of the present invention, a communication system is provided for connecting in real-time an Internet-based network interface to a plurality of backend systems, each of the plurality of backend systems having an associated backend communications protocol and requiring an associated backend data format. The system includes means for receiving a job having a front-end communications protocol and a front-end data format from the Internet-based network interface; means for selecting one or more backend systems from the plurality of backend systems as a function of attributes of the job for delivery of the job to the one or more backend systems; means for delivering the job to each of the one or more backend systems in the associated backend communications protocol and associated backend data format for each of the one or more backend systems; means for translating a response from each of the one or more backend systems from the associated backend communications protocol to the front-end communications protocol and from the associated backend data format to the front-end data format; and means for delivering a translated response to the Internet-based network interface.

BRIEF DESCRIPTION OF THE DRAWINGS

For the purpose of illustrating the invention, the drawings show a form of the invention that is presently preferred. However, it should be understood that the present invention is not limited to the precise arrangements and instrumentalities shown in the drawings, wherein.

DETAILED DESCRIPTION OF THE INVENTION

Figure 1:
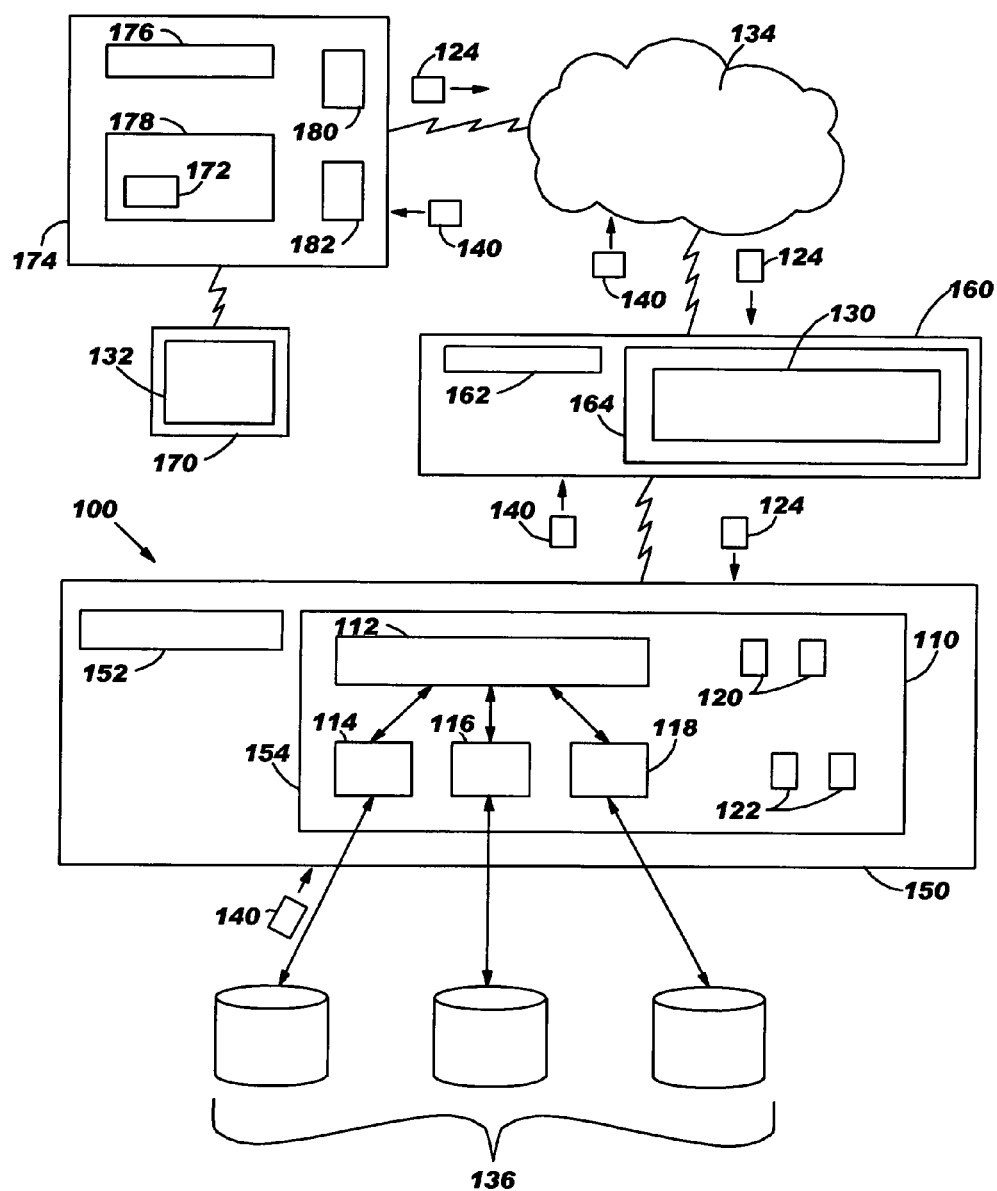
FIG. 1 is a schematic diagram of one example of a computing environment for a system according to the present invention.

Referring to FIG. 1, in one embodiment, the present invention provides a system 100 for connecting in real-time an Internet-based network interface to a plurality of backend systems. FIG. 1 illustrates in an appropriate computing environment in which system 100, and its communication system 110 may be used. Communication system 110 is discussed further in detail in FIG. 2, with examples of specific implementations in FIG. 4 and FIG. 5.

System 110 includes a router 112 in communication with a plurality of service agents 114, 116, and 118. System 110 can include one or more helper objects 120 and one or more format translation objects 122, each of which can communicate with the plurality of service agents 114, 116, and 118. As discussed further below, router 112 receives a job 124 from an Internet-based network interface 130. Typically, job 124 includes information input via a graphical user interface 132 in communication with an Internet-based network 134. The information is related to, and is intended for communication with, one or more of a plurality of backend systems 136. Each of plurality of backend systems 136 is associated with one of plurality of service agents 114, 116, and 118. This association is typically predefined at the time of configuring system 110. Examples of information contained in a job 124 according to the present invention include, but are not limited to, data for entry in one or more of a plurality of backend systems 136 and a query for information stored in one or more of a plurality of backend systems 136.

Router 112 selects one or more of said plurality of backend systems 136 to which to communicate job 124. Router 112 makes this selection based on attributes of job 124 and the information contained therein. The attributes of job 124 typically include information that indicates, when referenced against configuration information, which of backend systems 136 are implicated by job 124, for example which of backend systems 136 have data being requested by job 124. Router 112 then communicates job 124 to each of those service agents 114, 116, and 118 that are associated with the selected backend systems 136 for translation, reformatting, and communication to such backend systems. Each of the selected backend systems 136 processes job 124 and communicates a response 140 to the appropriate service agents 114, 116, and 118 for translation, reformatting, and communication to Internet-based network interface 130. Internet-based network interface 130 typically communicates response 140 to graphical user interface 132 for display.

FIG. 1 shows three service agents 114, 116 and 118 and three backend systems 136. However, a person of ordinary skill in the art will understand from the present invention that any number of service agents and backend systems can be employed.

FIG. 1 illustrates system 110 in an exemplary computing environment. Although not required, the invention will be described generally in terms of computer-executable instructions, typically included in program modules, that are executed by a conventional, general purpose computing device, such as a server. In one example, system 110 includes a server 150 for executing instructions in the program modules, as described more below. Server 150 typically includes a processor 152 and memory 154. In the example shown in FIG. 1, system 110 resides in memory 154. Server 150 is in communication with backend systems 136.

Backend systems 136 typically reside in memory of a server having a processor. An example of backend systems 136 include, but are not limited to, a database. When backend system 136 is a database, the backend system typically includes information, such as data. It is contemplated that an individual backend system 136 or multiple backend systems may reside on a single server, although multiple servers may be used in certain distributed computing environments. A single application programming interface (API) is typically used to communicate with each backend system 136.

Referring again to FIG. 1, Internet-based network interface 130 is executed by server 160. Server 160 typically includes a processor 162 and memory 164. Internet-based network interface 130 resides in memory 164. The example shown in FIG. 1 illustrates system 110 and Internet-based network interface 130 on different servers. However, a person of ordinary skill in the art will recognize that system 110 and Internet-based network interface 130 can reside on one server. Server 160 is in communication with Internet-based network 134. Internet-based network 134 is generally a global communication network, such as the Internet and its predecessors, or a network that includes a segment of a global communication network.

Graphical user interface 132 is typically displayed on a display device 170 of a computing device 174 using a browser object 172, such as a web browser. Computing device 174 typically includes processor 176; memory 178, in which browser object 172 resides; input device 180, such as a keyboard and/or a pointing device; and display controller 182. Examples of computing devices that are contemplated to display information from the system of the present invention include, but are not limited to, a personal computer, a terminal, a thin-client device, a personal data assistant (PDA), a mobile communication device, kiosks, appliances, and any combinations thereof.

Typically, Internet-based network interface 130, system 110, and backend systems 136 reside within a facility, such as a healthcare facility. The Internet-based network interface 130 in one example connects to the Internet. Remote users, such as clients and remote care providers, can connect to the various backend systems 136 using a browser object 172, such as a web browser. Typically, a healthcare facility will have one or more clinical backend systems 136 and one or more administrative backend systems (often from different vendors) that a particular remote user will have a need to access.

System 110 provides several benefits. System 110 allows the remote user to communicate using one interface 132, a web interface for example, with multiple types of healthcare information technology systems (e.g. clinical and administrative) having heterogeneous data formats that communicate with external systems using different protocols. The communication is in real-time without the creation of an intermediate database and duplicated data that can be inaccurate. Real-time describes an application that requires a process to respond to inputs while the application waits for the result. Typically, the process involves retrieval or filing of data. In this case, interface 132 makes a request or posts information through system 110 directly to one or more of backend systems 136 while the interface 132 waits for the result 140. Any changes made to the active databases of a backend system are instantaneously available to the remote user. The response time should be on the order of about 2 seconds or less, although somewhat longer response times fall within the meaning of "real time." System 110 of the present invention connects to one or more actual backend systems 136 in real time. In one aspect, this real time communication occurs without the use of an intermediate database that replicates information from the backend systems for the purpose of providing that information through the replicated database to users via an Internet interface. System 110 also permits a user to instigate repeated real-time jobs accessing information on different backend systems 136 and display the information using the same user interface 132. The security of any data is provided by and maintained by each of the backend systems 136, eliminating any intermediate management of security provisions.

Figure 2:
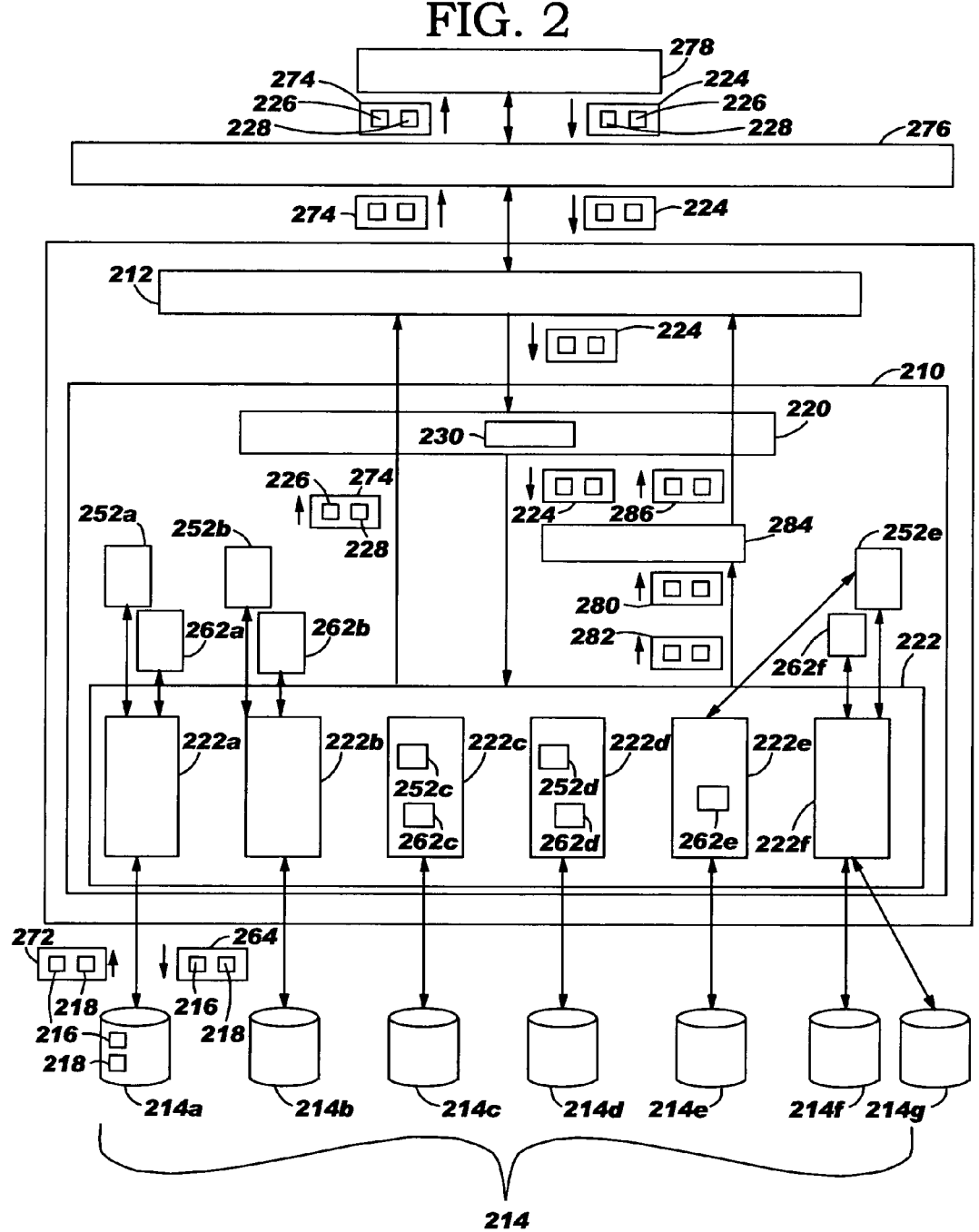
FIG. 2 is a schematic diagram of one example of a system according to the present invention.

Referring now to FIG. 2, in one embodiment of the present invention, a communication system 210 for connecting in real-time an Internet-based network interface 212 to a plurality of backend systems 214 is illustrated. System 210 is a more detailed depiction of system 110. Each of the plurality of backend systems 214 has an associated backend communications protocol 216 and requires an associated backend data format 218. System 210 includes a router 220 and a plurality of service agents 222. Examples of backend communications protocols 216 used by typical backend systems 214 include, but are not limited to, simple object access protocol (SOAP)-based web service, HTTP-based, ACTIVE-X data objects (ADO), open database connectivity (ODBC), and Transmission Control Protocol/Internet Protocol (TCP/IP).

Backend data formats 218 vary greatly from backend system 214 to backend system 214. For example, each backend system 214 may arrange information in different orders, require queries in a certain format, and/or label fields in which data is stored with different terms. These variances exist within products from the same vendor, but are exacerbated when products are from different vendors. Although, backend data formats 218 are complexly varied, each may be based on a common underlying structure, such as extensible markup language (XML)-based formats, onto which the complexity or propriety is built.

Referring again to FIG. 2, router 220 receives a job 224 having a front-end communications protocol 226 and a front-end data format 228 from the Internet-based network interface 212. Router 220 selects one or more of the plurality of backend systems 214 as a function of attributes of job 224. Typically, router 220 includes routing table 230 for selecting which of plurality of backend systems 214 are implicated by the attributes of the information included in job 224. Routing table 230 typically includes a table of information relating certain types of information that job 224 may include to the particular information included in each of backend systems 214, and provides the relationship that allows the router to direct job 224 to the appropriate backend system 214. Such attributes of job 224 indicate which of the plurality of backend systems 214 should be communicated job 224 for execution. In one example, router table 230 categorizes job attributes, and links the categories to service agents 222 that can handle those jobs (set up during configuration). When a job, such as sob 224, is submitted to router 220, the attributes are compared to table 230 to determine the category, which will in turn reveal the list of appropriate service agents 222. Router 230 then forwards the job on to the one or more service agents 222.

As stated above, job 224 can include, for example, information such as data for entry in one or more of the plurality of backend systems 214 or a query for response information from one or more of the plurality of the backend systems 214. If, for example, job 224 includes a query for a certain type of clinical information, router 220 may use routing table 230 to determine which of plurality of backend systems 214 have that certain type of clinical information.

The front-end communications protocol 226 according to the present invention is typically hyper text transfer protocol (HTTP). Front-end communications protocol 226 may be other standard front-end communication protocols including, but not limited to, HTTP, component object model (COM), and .NET.

The front-end data format 228 according to the present invention is generally one that supports information being entered by a user and the display of response information, such that the response information can be displayed through the Internet-based network interface 212, for example using a browser object 276, to the user. Front-end data format 228 is typically a standard data format, although proprietary formats may be used in some applications. Examples of standard data formats for use as a front-end data format 228 include, but are not limited to, XML-based format, such as HL-7 standard; delimited strings, and position-based strings.

Each of backend systems 214 is associated with at least one of the plurality of service agents 222. For example, in FIG. 2, service agents 222a, 222b, 222c, 222d, 222e, and 222f are each associated with, respectively, backend systems 214a, 214b, 214c, 214c, 214d, and 214e. Service agent 222f is also associated with backend system 249. The association of a service agent 222 with a backend system 214 typically occurs during the configuration of system 210 and is part of configuration files in router 220. Each of service agents 222 can communicate with router 220 and can translate a particular job, such as job 224, received from router 220 from front-end data format 228 to the associated backend data format 218 of the backend system associated with the individual service agent. The translation occurs using methods that are known to one of ordinary skill in the art. An example of a translation mechanism for handling transforms includes, but is not limited to, extensible stylesheet language transformations (XSLT). Configuration of translation mechanisms, such as XSLT can occur during the configuration of the system 210.

In one aspect, system 210 can also include a format translation object 252 in communication with plurality of service agents 222. Format translation object 252 includes computer-executable code, often in the form of a module, configured to assist a particular one of service agents 222 in translating to and from the associated backend data format 218 of a particular backend system 214. A format translation object 252 can be separate from service agents 222 or can be included in a particular one of service agents 222. For example, service agents 222c and 222d include format translation objects 252c and 252d, respectively. Although, format translation objects 252 according the present invention are generally used for both to and from translation, it is contemplated that a separate format translation object would be used for translation to a particular backend data format 218 and another format translation object would be used for translation from that particular backend data format.

Example system 210 includes format translation objects 252a, 252b, and 252e separate from backend systems 214. It should be noted that a system according to the present invention can have any number of format translation objects 252. A person of ordinary skill in the art will be able to determine the appropriate number of format translation objects 252 required for a particular system based on the number of known and/or required backend data formats 218. It should also be noted that a particular format translation object 252 may also be utilized by more than one service agent 222. For example, in FIG. 2, service agents 238 and 240 each utilize format translation object 252e. This situation may possibly arise where two or more backend systems 214, in this example backend systems 214e, 214f, and 214g, have identical required backend data formats 218.

Each of service agents 222 can also translate a job, such as job 224, from front-end communications protocol 226 to the associated backend communications protocol 216 of the backend system 214 associated with the individual service agent. In another aspect, system 210 can also include a helper objects 262 in communication with plurality of service agents 222. Helper objects 262 includes computer-executable code, often in the form of a module, configured to assist a particular one of plurality of service agents 222 in translating to and from the associated backend communications protocol 216 of a particular backend system. Helper objects 262 assist in translation by having code that knows exactly how to communicate on a certain protocol. Helper objects 262 can remain available for use by any service agent 222. Helper object 262 assists service agent 222 by serving as a communication "proxy" for service agent 262. Instead of service agent 222 implementing code to talk on the necessary protocol, the service agent simply invokes helper object 262, which knows how to talk on the protocol inherently. A helper object 222 can be separate from plurality of service agents 222 or can be included in a particular one or plurality of service agents 222. For example, service agents 222c, 222d, and 222e include helper objects 262c, 262d, and 262e, respectively.

Example system 210 also illustrates helper objects 262a, 262b, and 262f. It should be noted that a system according to the present invention can have any number of helper objects. A person of ordinary skill in the art will be able to determine the appropriate number of helper objects required for a particular system based on the number of known and/or required backend communications protocols. It should also be noted that a particular helper object may also be utilized by more than one service agent. This situation may possibly arise where two or more backend systems have identical required backend communications protocols. Although, helper objects according the present invention are generally used for both to and from translation, it is contemplated that a separate helper object would be used for translation to a particular backend communications protocol and another helper object would be used for translation from that particular backend communications protocol.

With continuing reference to FIG. 2, each of plurality of service agents 222 can also communicate a translated job, such as translated job 264 to the associated one of plurality of backend systems 214 and receive a response, for example response 272 having associated backend communications protocol 216 and associated backend data format 218, from the associated one of the plurality of backend systems 214. Each of plurality of service agents 222 can also translate a response, such as response 272, from the associated backend communications protocol 216 to the front-end communications protocol 216, and translate a response, such as response 272, from the associated backend communications protocol to said front-end communications protocol. Each of plurality of service agents 222 can utilize communication with a helper object 252 and/or a format translation object 262, as discussed above to assist with such translation. Further, each of plurality of service agents 222 can communicate a translated response 274 to Internet-based network interface 212. In one aspect, the communication of translated response 274 may occur directly from each of plurality of service agents 222 to Internet-based network interface 212. In another aspect, the communication of translated response 274 from each of plurality of service agents 222 to Internet-based network interface 212 may occur as a passive pass through of router 220. In still another aspect, translated response 274 may be communicated from Internet-based network interface 212 to browser object 276, such as an Internet web browser. In yet another aspect, translated response 274 may be communicated by browser object 276 in the form of graphical user interface 278.

In a further aspect, job 224 may include information that is related to two or more of plurality of backend systems 214, such that router 220 communicates job 224 to two or more of plurality of service agents 222. In such a case, a plurality of translated responses (such as a first translated response 280 and a second translated response 282) may be produced by plurality of service agents 222. Thus, system 210 may include a merger object 284 configured to receive translated result 274 from plurality of service agents 222, to merge first translated response 280 from a first of plurality of backend systems 214 with a second translated response 282 from a second of plurality of backend systems into a combined response 286 prior to communicating first response 282 and second response 284 to Internet-based network interface 212, and to communicate combined response 286 to Internet-based network interface 212. Merger object 284 may include computer executable instructions for merging a plurality of responses into a combined response. Such computer executable instructions for merging are well known to persons skilled in the art. Merger object 284 uses processes that are well known to one of ordinary skill in the art to merge two or more responses into a combined response 286. In one example, two or more XML responses are merged into a single XML stream using XSLT and specialized object code.

Each of the plurality of service agents, helper objects, format translation objects, and router are configurable to provide information related to each of the plurality of backend servers that are used at a particular facility.

Figure 3:
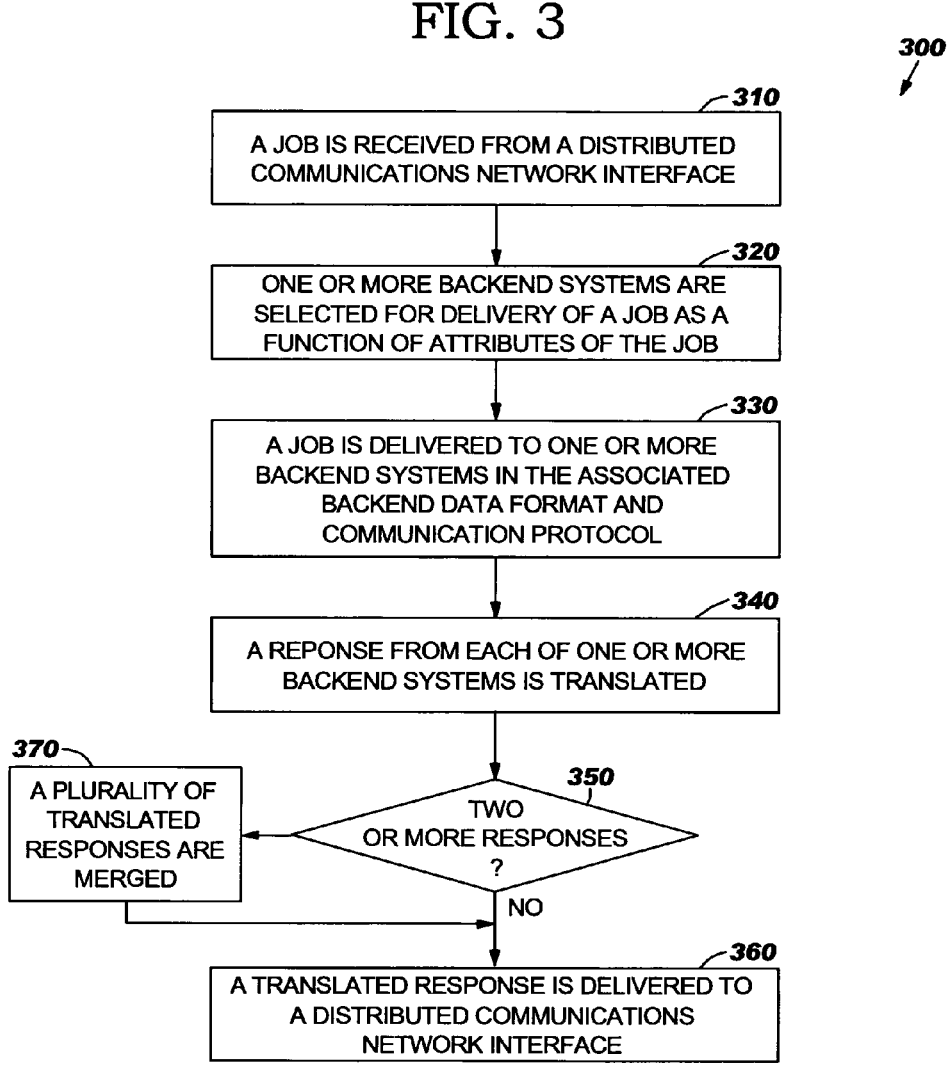
FIG. 3 is a flow chart of one example of a method according to the present invention.

Operation of system 210 is described below in connection with the flow diagram of FIG. 3 First, at step 310, a job 224 having a front-end communications protocol 226 and a front-end data format 228 from the Internet-based network interface 212 is received. In one example, the job is received by a router, such as router 220. Then, at step 320, one or more backend systems are selected as a function of attributes of the job from the plurality of backend systems for delivery of the job to the one or more backend systems. In one example, the selecting of step 320 is performed by a router, such as router 220, using a routing table, such as routing table 230. Next, at step 330, the job is delivered to each of the one or more backend systems in the associated backend communications protocol and associated backend data format for each of the one or more backend systems. In one aspect, the job is delivered by one of a plurality of service agents, (such as plurality of service agents 222), which translate, as discussed above, the front-end communications protocol to the associated backend protocol and translate the front-end data format to the associated backend data format prior to delivering to the associated one or more backend systems. Then, at step 340, a response (such as response 272) from each of the one or more backend systems is translated, for example by one of the plurality of service agents, from the associated backend communications protocol to the front-end communications protocol and from the associated backend data format to the front-end data format. Next, at 350, if only one translated response (such as translated response 274) is generated it is delivered in step 360, for example by one of the plurality of service agents, to the Internet-based network interface. In one aspect, step 370 may be implemented prior to delivering the translated response to the Internet-based network interface when two or more backend systems each produce a response. In step 370, a first translated response from a first of the one or more backend systems is merged (for example, by a merger object, such as merger object 284) with a second translated response from a second of said one or more backend systems into a combined response (such as combined response 286).

Figure 4:
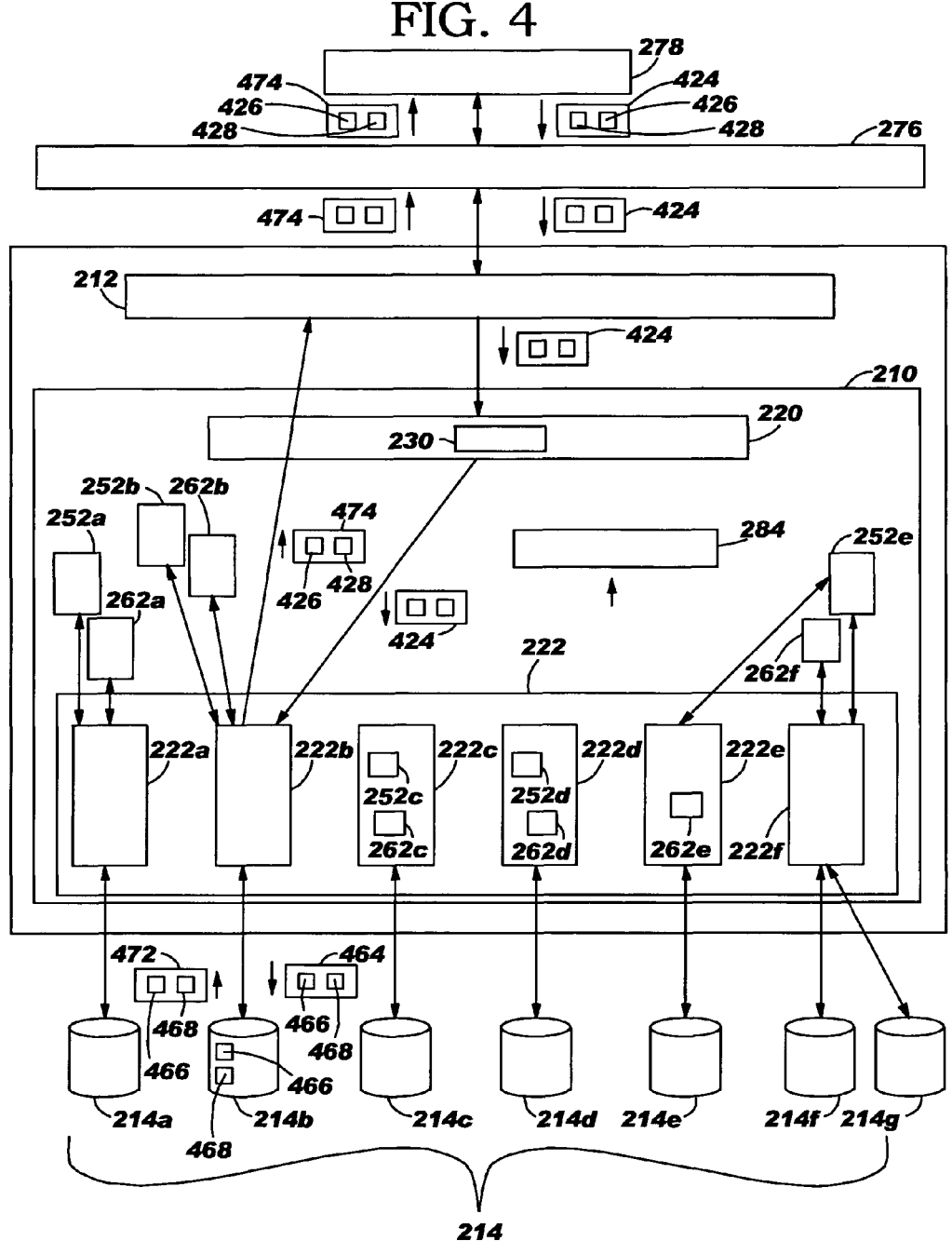
FIG. 4 is a schematic diagram of another example of a system and method according to the present invention.

Turning now to FIG. 4, one example of the application of the system of FIG. 2 and method of the present invention is provided. A job 424 is input by a remote user via graphical user interface 278 and browser object 276, and communicated to Internet-based network interface 212. Job 424 having front-end communications protocol 426 and front-end data format 428 is communicated to router 220 of system 210. Router 220 compares the information contained in job 424 (for example a query for medications prescribed to patient X, a patient of a large healthcare enterprise having a plurality of backend systems 214) to router table 230. Plurality of backend systems 214 include backend systems 214a, 214b, 214c, 214d, 214e, 214f, and 214g. Router table 230 includes metadata including configuration information related to each of plurality of backend systems 214, the data stored on each of plurality of backend systems 214, and the type of requests or data input each of plurality of backend systems 214 can handle. Router 220 determines which of plurality of backend systems 214 has information related to medications for patients. In this case backend system 214b has information related to medications for patients. System 210 includes a plurality of service agents 222. Plurality of service agents 222 includes service agents 222a, 222b, 222c, 222d, 222e, and 222f, each of which is associated with one of backend systems 214a, 214b, 214c, 214d, 214e, 214f, and 214g, respectively. Router 220 communicates job 424 to service agent 222b, which is associated with backend system 214b. Backend system 214b has backend communications protocol 466 and requires backend data format 468. Service agent 214b communicates with helper object 262b to translate front-end communications protocol 426 to backend communications protocol 466. Helper object 262b is one of a plurality of helper objects 262 included in system 210. Helper object 262b includes computer executable instructions for translating the front-end communications protocol 426 to and from backend communications protocol 466. Service agent 222b also communicates with format translation object 252b to translate front-end data format 428 to backend data format 468. Format translation object 252b is one of a plurality of format translation objects 252 included in system 210. Format translation object 252b includes computer executable instructions for translating the front-end data format 428 to backend data format 468.

Service agent 222b then communicates a translated job 464 to backend system 214b. Backend system 214b executes translated job 464 and communicates a response 472 to service agent 222b. Response 472 includes information, for example a list of prescribed medications for patient X, and is in backend communications protocol 466 and backend data format 468. Service agent 222b then translates, as described above, response 472 to front-end communications protocol 426 and front-end data format 428. Service agent 422b communicates a translated response 474 to Internet-based network interface 212, in this case as a passive pass through of router 220. Translated response 474 is then displayed via graphical user interface 278 and browser object 276.

Figure 5:
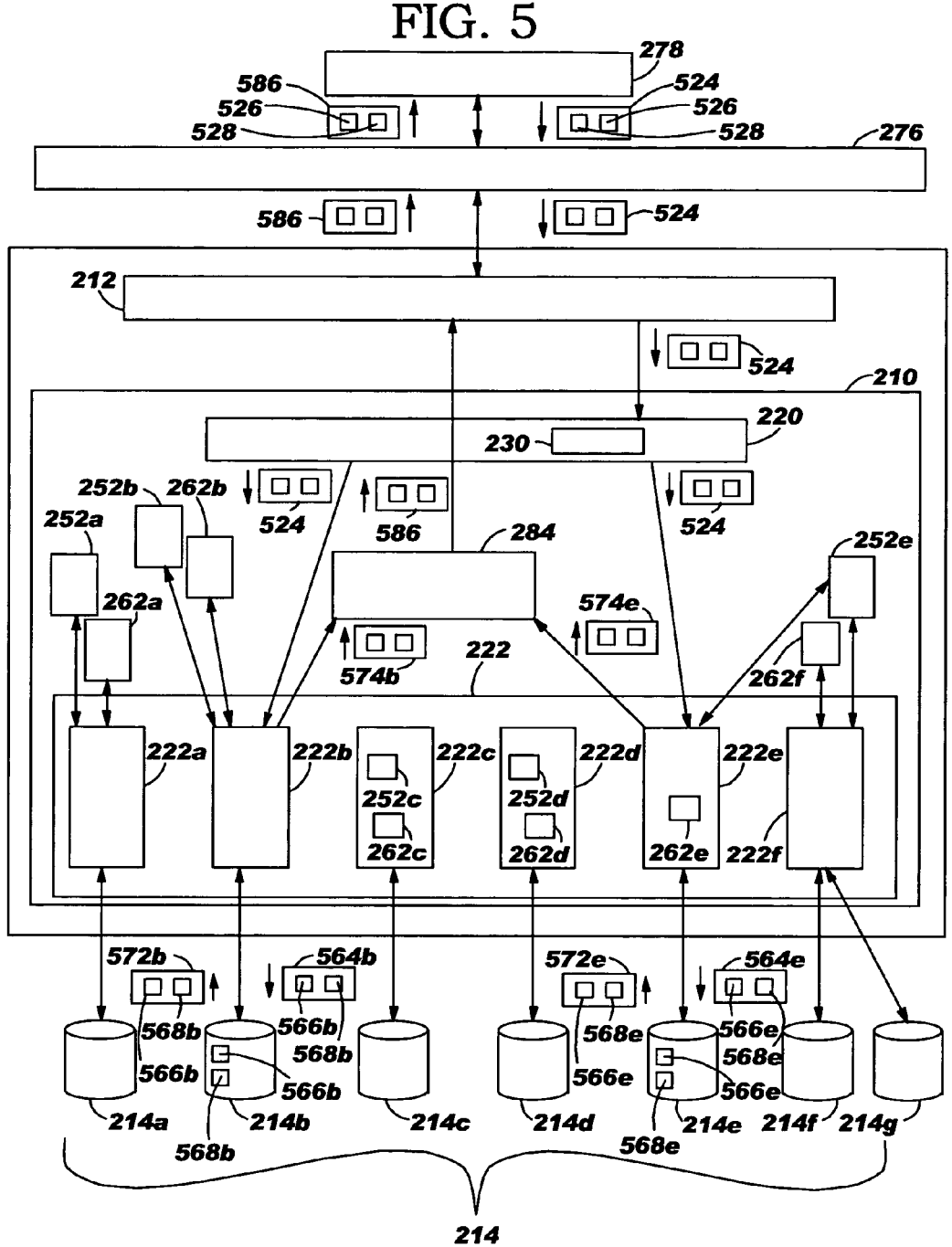
FIG. 5 is a schematic diagram of still another example of a system and method according to the present invention.

Turning now to FIG. 5, another example of the application of the system of FIG. 2 and method of the present invention is provided. A job 524 is input by a remote user via graphical user interface 278 and browser object 276, and communicated to Internet-based network interface 212. Job 524 having front-end communications protocol 526 and front-end data format 528 is communicated to router 220 of system 210. Router 220 compares the information contained in job 524 (for example a query for medications prescribed to patient Y, a patient of a large healthcare enterprise having a plurality of backend systems 214) to router table 230. Router 220 determines which of plurality of backend systems 214 has information related to medications for patients. In this case backend system 214b and backend system 214e have information related to medications for patients. Router 220 communicates job 524 to service agents 222b and 222e, which are associated with backend systems 214b and 214e, respectively. Backend system 214b has backend communications protocol 566b and requires backend data format 568b. Backend system 214e has backend communications protocol 566e and requires backend data format 568e.

Service agent 222b communicates with helper object 262b to translate job 524 from front-end communications protocol 526 to backend communications protocol 566b. Service agent 222b also communicates with format translation object 252b to translate front-end data format 528 to backend data format 568b.

Service agent 222e communicates with helper object 262e to translate job 524 from front-end communications protocol 526 to backend communications protocol 266e. Helper object 262e is embedded code within service agent 222e. Service agent 222e also communicates with format translation object 252e to translate front-end data format 528 to backend data format 568e.

Service agent 222b communicates a translated job 564b to backend system 214b. Backend system 214b executes translated job 564b and communicates a response 572b to service agent 222b. Response 572b includes information, for example a list of prescribed medications for patient Y, and is in backend communications protocol 566b and backend data format 568b. Service agent 222b then translates, as described above, response 572b to front-end communications protocol 526 and front-end data format 528. Service agent 222b communicates a translated response 574b to merger object 284.

Service agent 222e communicates a translated job 564e to backend system 214e. Backend system 214e executes translated job 564e and communicates a response 572e to service agent 222e. Response 572e includes information, for example a list of prescribed medications for patient Y, and is in backend communications protocol 566e and backend data format 568e. Service agent 222e then translates, as described above, response 572e to front-end communications protocol 526 and front-end data format 528. Service agent 222e communicates a translated response 574e to merger object 284.

Merger object 284 includes computer executable instructions for merging translated response 574b and translated response 574e. Merger object 284 merges translated responses 574b and 574e to a combined response 586. Merger object 284 communicates combined response 586 in front-end communications protocol 526 and front-end data format 528 to Internet-based network interface 212, in this case directly to Internet-based network interface 212. Combined response 586 includes information from each of backend systems 214b and 214e that is related to job 524, for example a merged list of medications for patient Y. Combined response 586 is then displayed via graphical user interface 278 and browser object 276.

Figure 6:
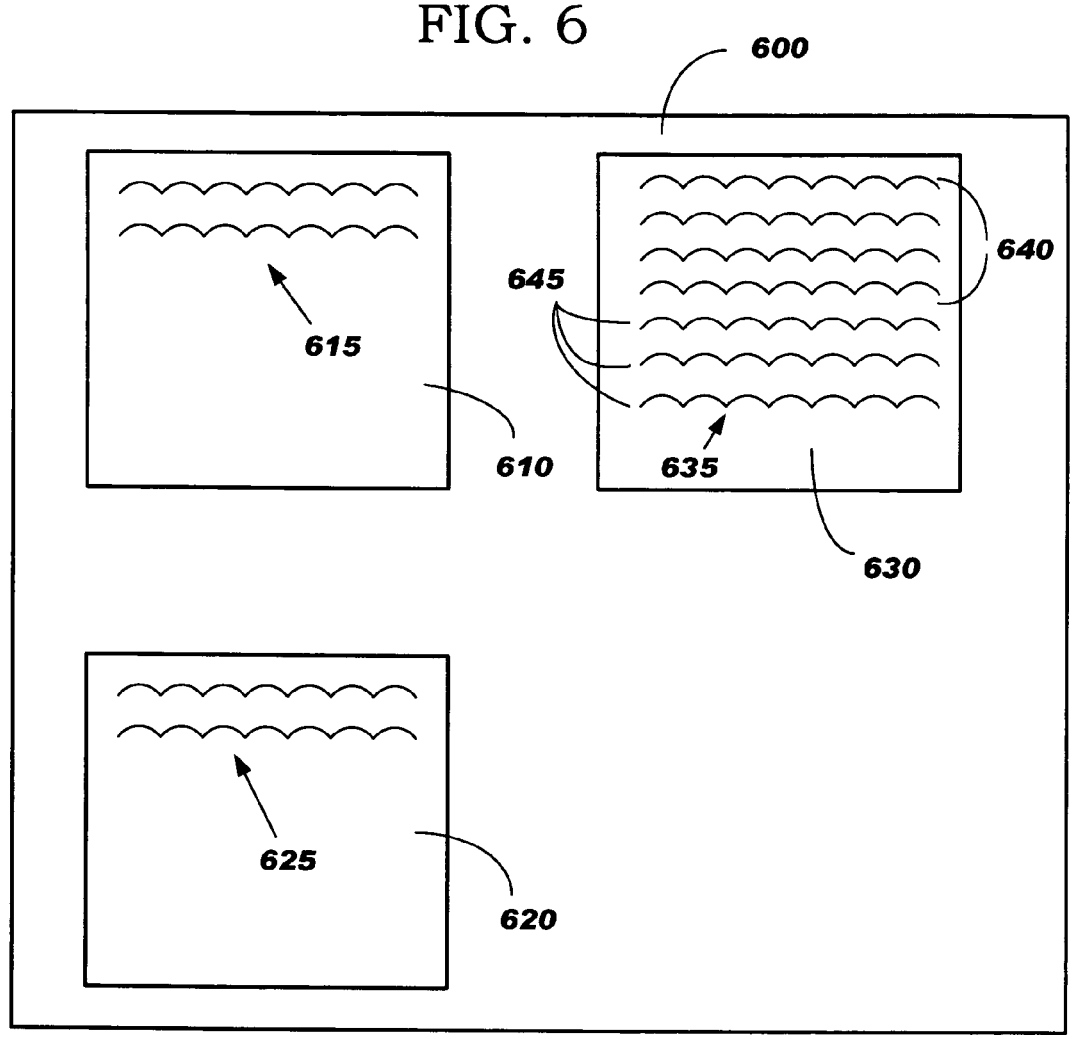
FIG. 6 is a schematic diagram of one example of a graphical user interface according to the present invention.

Another aspect of the present invention is a graphical user interface for use in a system for connecting in real-time an Internet-based network interface (such as Internet-based network interface 212) and a plurality of backend systems (such as plurality of backend systems 214), each of the plurality of backend systems having an associated backend communications protocol (such as backend communications protocol 216) and requiring an associated backend data format (such as backend data format 218). Turning now to FIG. 6, graphical user interface 600 includes a first portion 610 showing first information 615 from a first one of the plurality of backend systems and a second portion 620 showing second information 625 from a second one of the plurality of backend systems. FIG. 6 also illustrates a third portion 630 showing merged information 635 merged from a fourth-information 640 from a fourth one of the plurality of backend systems and a fifth information 645 from a fifth one of the plurality of backend systems. In another aspect, graphical user interface 278 is displayed using a browser object, such as browser object 276.

Figure 7:
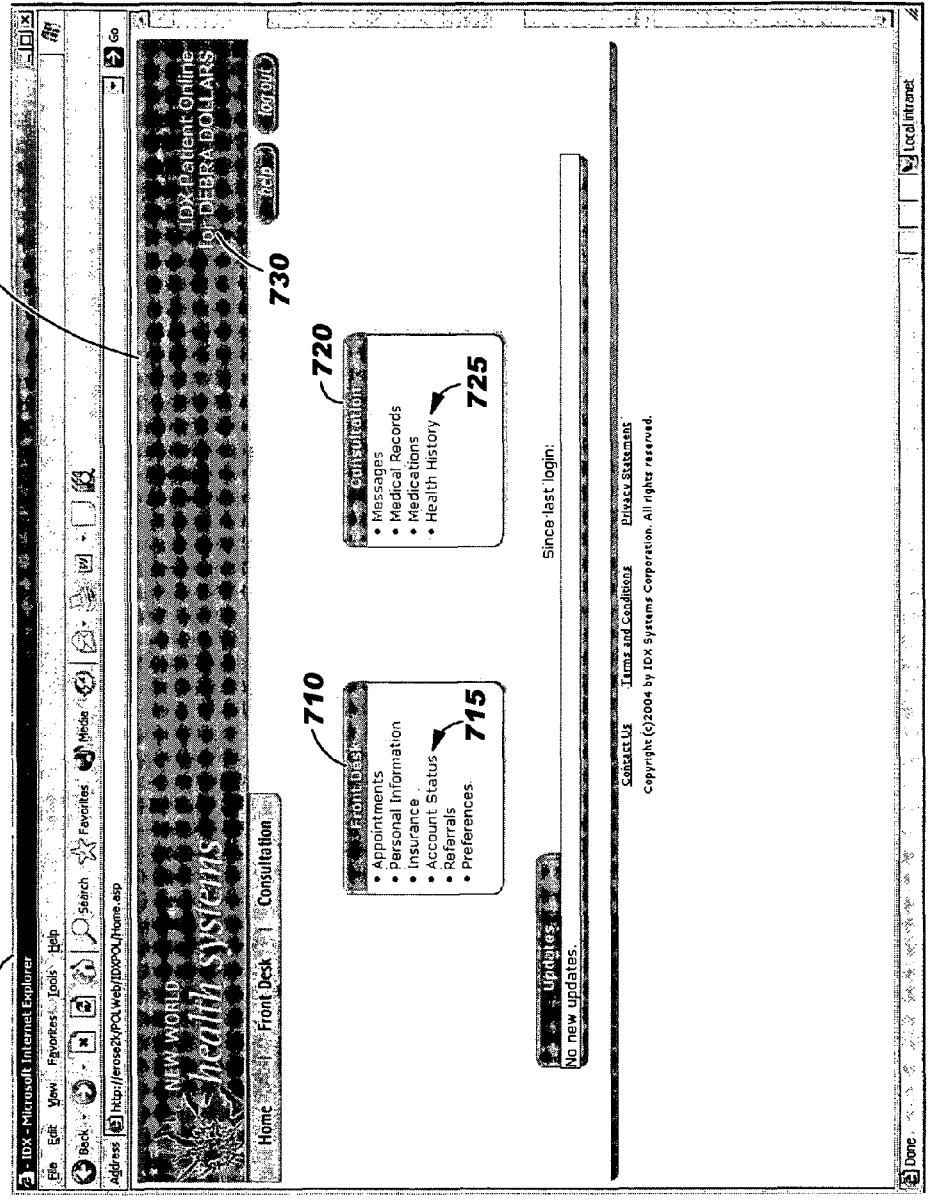
FIG. 7 is a screen captured representation of another example of a graphical user interface according to the present invention.

Turning now to FIG. 7, one example of a graphical user interface 700 according to the present invention is provided. Graphical user interface 700 is displayed using a browser object 705, in this case the web browser INTERNET EXPLORER available from MICROSOFT. Graphical user interface 700 includes a first portion 710 displaying a first menu information 715 and a second portion 720 displaying a second menu information 725, each for example representing information about a given patient "Debra Dollars" 730. First menu information 715 is communicated to graphical user interface 700 via an Internet-based network interface (in this case IDX Systems Corporation's PATIENT ONLINE system) from a first backend system dedicated to administrative information of a healthcare facility (in this case IDX Systems Corporation's FLOWCAST system). Second menu information 725 is communicated to graphical user interface via the same Internet-based network interface from second backend system dedicated to clinical information of the same healthcare facility. First backend system and second backend system have different communications protocols and require different data formats.

Figure 8:
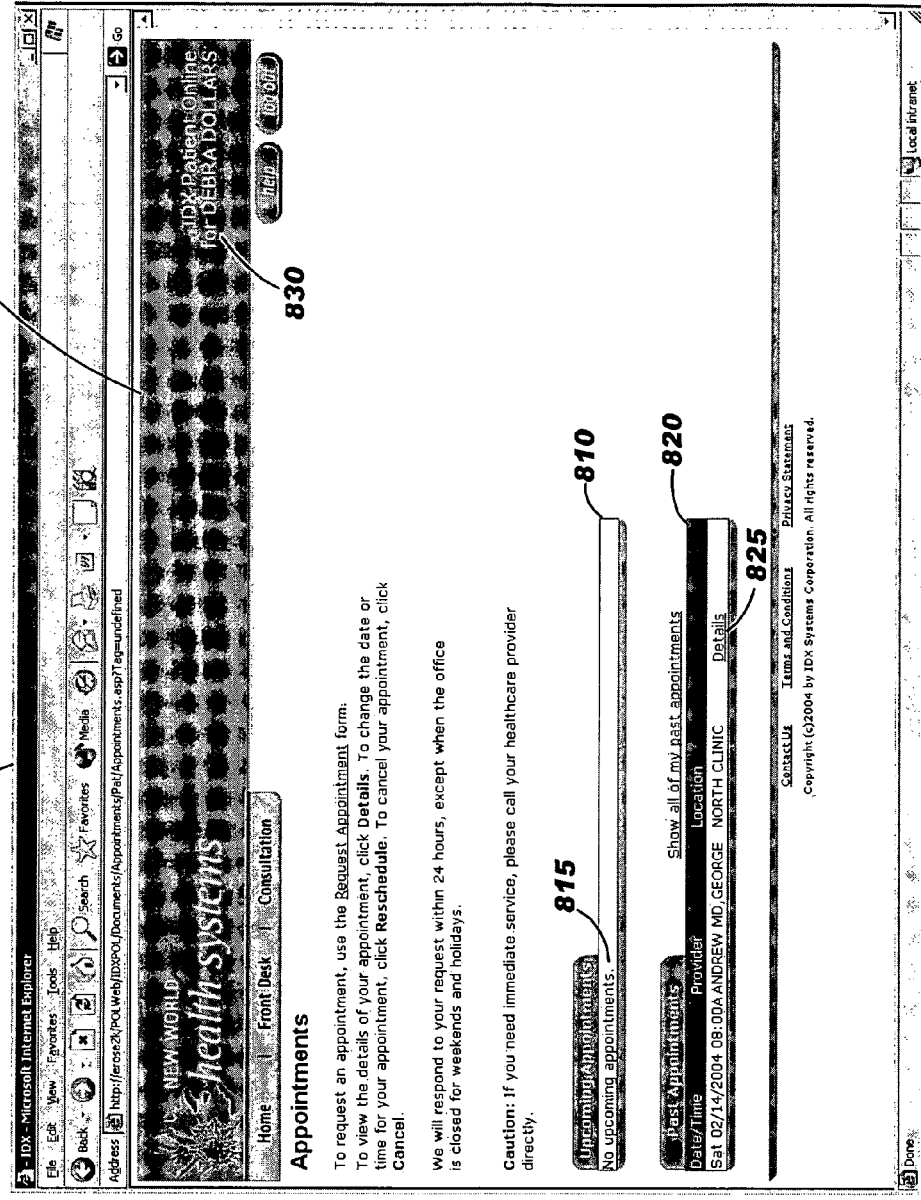
FIG. 8 is a screen captured representation of still another example of a graphical user interface according to the present invention.

A user of graphical user interface 700 who is remote from the healthcare facility can access information from each of first and second backend systems in real-time. For example, if a user were to select the "Appointments" information item from first portion 710, a job (such as job 224) will be communicated to a system according to the present invention (such as system 210), a response (such as response 274) will be returned in real-time from one or more administrative backend systems (in this case the FLOWCAST system) through the Internet-based network interface, and graphical user interface 800 in FIG. 8 would be displayed. Graphical user interface 800 includes a first portion 810 having future appointment information 815 and a second portion 820 having past appointment information 825, each for patient 830, "Debra Dollars."

Figure 9:
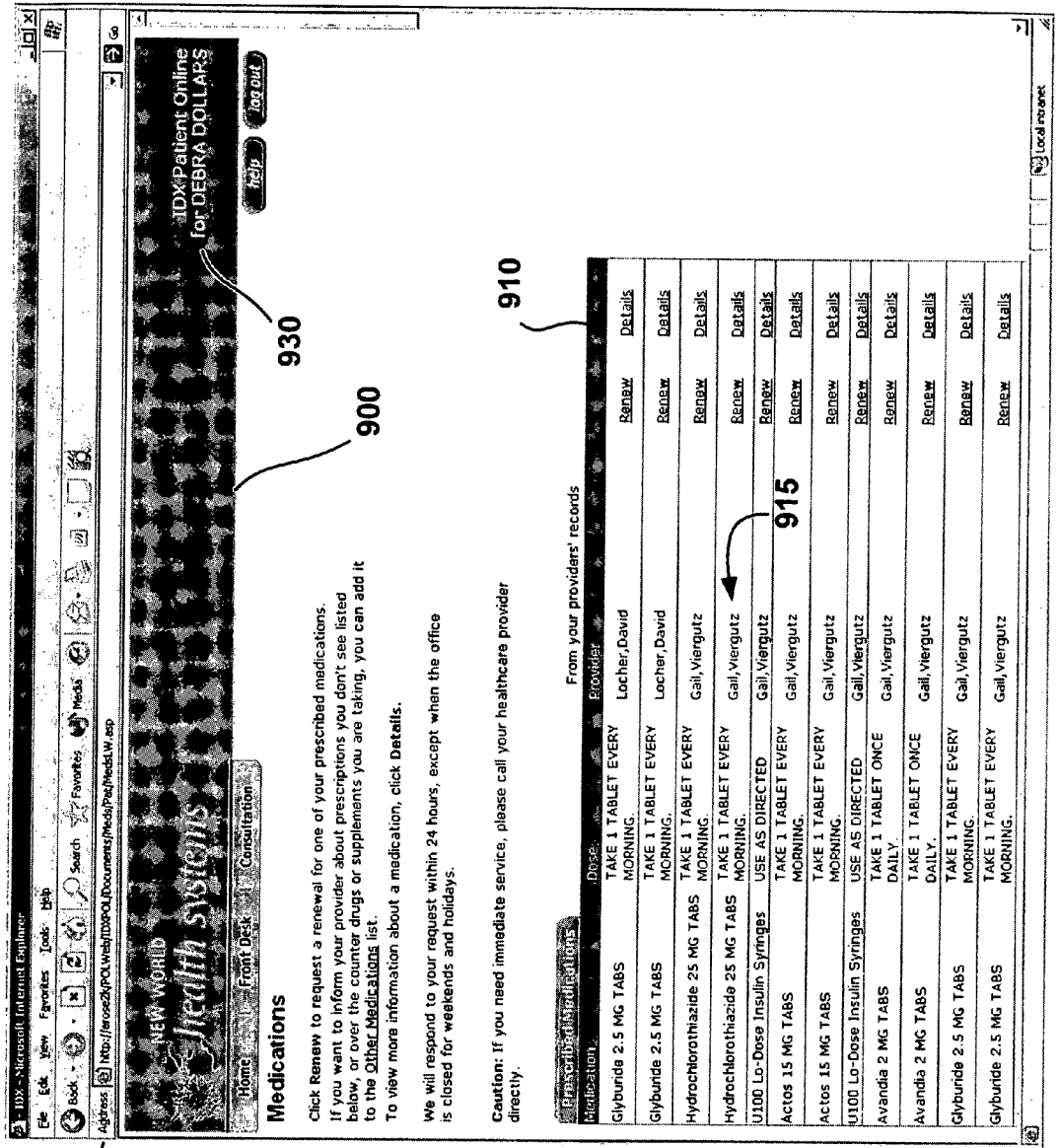
FIG. 9 is a screen captured representation of yet another example of a graphical user interface according to the present invention.

Referring again to FIG. 7, in another example, if a user were to select the "Medications" information item from second portion 720 a job will be communicated to the system, a response will be returned in real-time from one or more clinical backend systems through the Internet-based network interface, and graphical user interface 900 in FIG. 9 would be displayed. Graphical user interface 900 includes first portion 910 having medication information 915 for patient 930, "Debra Dollars."

Although the invention has been described and illustrated with respect to [an] exemplary embodiment[s] thereof, it should be understood by those skilled in the art that the foregoing and various other changes, omissions and additions may be made therein and thereto, without parting from the spirit and scope of the present invention.

What is claimed is:

1. A communication system for connecting in real-time, the system comprising:
   an Internet-based network interface;
   a server coupled with the Internet-based network interface;
   a plurality of backend systems separate from and coupled with the server, each of the plurality of backend systems having an associated backend communications protocol and requiring an associated backend data format;
   a router configured in the server for receiving a job having a front-end data format and a front-end communications protocol from the Internet-based network interface, wherein said router selects one or more backend systems from said plurality of backend systems as a function of attributes of said job for delivery of said job to said one or more backend systems;
   a plurality of service agents configured in the server, each of the plurality of service agents being associated with a respective one of the plurality of backend systems, each of said plurality of service agents being configured (1) to translate said job received from said router from said front-end data format to the associated backend data format of the respective one of the plurality of back-end systems, (2) to translate said job from said front-end communications protocol to the associated backend communications protocol of the respective one of the plurality of back-end systems, (3) to communicate said job to the associated one of the plurality of backend systems, (4) to receive a response to said job from the associated one of the plurality of backend systems, (5) to translate said response from the associated backend communications protocol to said front-end communications protocol, (6) to translate said response to said job from the associated backend data format to said front-end data format, and (7) to communicate a translated response to said Internet-based network interface, wherein the translated response is communicated through the server to the Internet-based network interface;
   a helper object configured in the server and separate from the plurality of service agents and in communication with said plurality of service agents said helper object being operatively configured to assist said plurality of service agents in translating to and from the associated backend communications protocol; and
   a merger object configured in the server and operatively configured to receive said translated response from said plurality of service agents, to merge a first translated response from a first of said one or more backend systems with a second translated response from a second of said one or more backend systems into a combined response prior to communicating said first translated response and said second translated response to said Internet-based network interface, and to communicate said combined response to said Internet-based network interface.

2. A communication system according to claim 1, wherein the system does not include a database that replicates information from the plurality of backend systems.

3. A communications system according to claim 1, wherein said Internet-based network interface communicates with a browser object.

4. A communication system according to claim 3, wherein said front-end data format provides said translated response to said Internet-based network interface in such a format as to allow said browser object to display said translated response.

5. A communication system according to claim 1, wherein said plurality of service agents comprise a protocol translation object for translating to and from the associated backend communications protocol.

6. A communication system according to claim 1, further comprising a format translation object in communication with said plurality of service agents, said translation object being operatively configured to assist said plurality of service agents translating to and from the associated backend data format.

7. A communication system according to claim 1, wherein said plurality of service agents comprise a format translation object for translating to and from the associated backend data format.

8. A communication system according to claim 1, wherein said job comprises information related to said one or more selected backend systems and wherein said router comprises a routing table having relationships between said information and said plurality of backend systems.

9. A communication system for connecting in real-time, the system comprising:

an Internet-based network interface;

a server coupled with the Internet-based network interface;

a first backend system separate and coupled with the server, having a first backend communications protocol and requiring a first backend data format and a second backend system separate and coupled with the server, having a second backend communications protocol and requiring a second backend data format;

a router configured in the server for receiving a job having a front-end data format and a front-end communications protocol from the Internet-based network interface, wherein said router selects one or more backend systems from said first and second backend systems as a function of attributes of said job for delivery of said job to said one or more backend systems;

a first service agent configured in the server and associated with the first backend system and configured (1) to receive said job from said router, (2) to translate said job received from said router from said front-end data format to the first backend data format, (3) to translate said job from said front-end communications protocol to the first backend communications protocol, (4) to communicate said job to the first backend system, (5) to receive a first response to said job from the first backend systems, (6) to translate said first response to said job from the first backend communications protocol to said front-end communications protocol, (7) to translate said first response to said job from the first backend communications protocol to said front-end communications protocol, and (8) to communicate a first translated response to said Internet-based network interface through the server;

a second service agent configured in the server and associated with the second backend system and operatively configured (1) to receive said job from said router, (2) to translate said job received from said router from said front-end data format to the second backend data format, (3) to translate said job from said front-end communications protocol to the second backend communications protocol, (4) to communicate said job to the second backend system, (5) to receive a second response to said job from the second backend system, (6) to translate said second response to said job from the second backend communications protocol to said front-end communications protocol, (7) to translate said second response to said job from the second backend communications protocol to said front-end communications protocol, and (8) to communicate a second translated response to said Internet-based network interface through the server;

a helper object configured in the server and separate from the first and second service agents and in communication with both of the first and second service agents, said helper object being operatively configured to assist said first and second service agents in translating to and from the first and second back-end communications protocols:

a merger object configured in the server and operatively configured to receive said translated response from said first and second service agents, to merge said first translated response with said second translated response into a combined response prior to communicating said first translated response and said second translated response to said Internet-based network interface, and to communicate said combined response to said Internet-based network interface.

10. A communication system according to claim 9, wherein the system does not include a database that replicates information from the plurality of backend systems.

11. A communication system according to claim 9, wherein said Internet-based network interface communicates with a browser object.

12. A communication system according to claim 11, wherein said front-end format provides said first translated response and/or said second translated response to said Internet-based network interface in such a format as to allow said browser object to display said first translated response and/or said second translated response.

13. A communication system according to claim 9, wherein said job comprises information related to one or more selected backend systems and wherein said router comprises a routing table having relationships between said information and said first and second backend systems.

14. A method of communicating in real-time between an Internet-based network interface and a plurality of backend systems, each of the plurality of backend systems having an associated backend communications protocol and requiring an associated backend data format, the method comprising:

receiving into a server a job having a front-end communications protocol and a front-end data format from the Internet-based network interface;

selecting one or more backend systems from said plurality of backend systems as a function of attributes of said job for delivery of said job to said one or more backend systems;

translating said job into an associated back-end communications protocol of the selected one or more back-end systems with one of a plurality of service agents, wherein the one of a plurality of service agents is dedicated to the selected one or more back-end systems delivering said job to each of said selected one or more backend systems, wherein said job is delivered from the one of the plurality of service agents in the associated backend communications protocol and associated back-end data format for each of said selected one or more backend systems;

translating in the server a response to said job from each of said selected one or more backend systems from the associated backend communications protocol to said front-end communications protocol and from the associated backend data format to said front-end data format, wherein a helper object is configured in the server and separate from the plurality of service agents, said helper object being configured to assist the plurality of service agents with translating to and from the associated back-end communications protocol;

merging in the server a first translated response from a first of said one or more selected backend systems with a second translated response from a second of said one or more selected backend systems into a combined response prior to communicating said first translated response and said second translated response to said Internet-based network interface; and delivering said combined response to said Internet-based network interface from the server.

15. A method according to claim 14, further comprising communicating said combined response from said Internet-based network interface to a browser object in communication with an Internet-based network.

16. A non-transitory computer readable medium having computer-executable instructions, for communicating in real-time between an Internet-based network interface and a plurality of backend systems, each of the plurality of backend systems having an associated backend communications protocol and requiring an associated backend data format, that when executed performs a method comprising the following steps:

receiving into a server a job having a front-end communications protocol and a front-end data format from the Internet-based network interface;

selecting one or more backend systems from said plurality of backend systems as a function of attributes of said job for delivery of said job to said one or more backend systems;

translating said job into an associated back-end communications protocol of the selected one or more back-end systems with one of a plurality of service agents, wherein the one of a plurality of service agents is dedicated to the selected one or more back-end systems delivering said job to each of said selected one or more backend systems, wherein said job is delivered from the one of the plurality of service agents in the associated backend communications protocol and associated back-end data format for each of said selected one or more backend systems;

translating in the server a response to said job from each of said selected one or more backend systems from the associated backend communications protocol to said front-end communications protocol and from the associated backend data format to said front-end data format, wherein a helper object is configured in the server and separate from the plurality of service agents, said helper object being configured to assist the plurality of service agents with translating to and from the associated back-end communications protocol;

merging in the server a first translated response from a first of said one or more selected backend systems with a second translated response from a second of said one or more selected backend systems into a combined response prior to communicating said first translated response and said second translated response to said Internet-based network interface; and delivering said combined response to said Internet-based network interface from the server.

17. A non-transitory computer readable medium according to claim 16, further comprising communicating said combined response from said Internet-based network interface to a browser object in communication with an Internet-based network.

18. A communication system for connecting real-time an Internet-based network interface to a plurality of backend systems, each of the plurality of backend systems having an associated backend communications protocol and requiring an associated backend data format, the system comprising:

means for receiving into a server a job having a front-end communications protocol and a front-end data format from the Internet-based network interface;

means for selecting one or more backend systems from said plurality of backend systems as a function of attributes of said job for delivery of said job to said one or more backend systems;

means for translating said lob into an associated back-end communications protocol of the selected one or more back-end systems with one of a plurality of service agents, wherein the one of a plurality of service agents is dedicated to the selected one or more back-end systems;

means for delivering said job to each of said selected one or more backend systems, wherein the delivery means delivers said job server from the one of the plurality of service agents in the associated backend communications protocol and associated backend data format for each of said selected one or more backend systems;

means for translating in the server a response to said job from each of said selected one or more backend systems from the associated backend communications protocol to said front-end communications protocol and from the associated backend data format to said front-end data format, wherein a helper object is configured in the server and separate from the plurality of service agents, said helper object being configured to assist the plurality of service agents with translating to and from the associated back-end communications protocol;

means for merging in the server a first translated response from a first of said selected one or more backend systems with a second translated response from a second of said selected one or more backend systems into a combined response prior to delivering said first translated response and said second translated response to said Internet-based network interface; and means for delivering said combined response to said Internet-based network interface from the server.

19. A communication system according to claim 18, further comprising means for communicating said combined response from said Internet-based network interface to a browser object in communication with an Internet-based network.

\* \* \* \* \*